(12) United States Patent
Gill

(10) Patent No.: US 8,696,763 B2
(45) Date of Patent: Apr. 15, 2014

(54) PROSTHETIC APPARATUS AND CONTROL METHOD

(75) Inventor: Hugh Gill, Gleniffer Gate (GB)

(73) Assignee: Touch EMAS Ltd., Livingston (GB)

( * ) Notice: Subject to any disclaimer, the term of this patent is extended or adjusted under 35 U.S.C. 154(b) by 37 days.

(21) Appl. No.: 13/387,166

(22) PCT Filed: Sep. 13, 2010

(86) PCT No.: PCT/GB2010/051529
§ 371 (c)(1),
(2), (4) Date: Jan. 26, 2012

(87) PCT Pub. No.: WO2011/036473
PCT Pub. Date: Mar. 31, 2011

(65) Prior Publication Data
US 2012/0123558 A1    May 17, 2012

(30) Foreign Application Priority Data
Sep. 25, 2009 (GB) .................................. 0916895.6

(51) Int. Cl.
*A61F 2/70* (2006.01)
*A61F 2/48* (2006.01)
*A61F 2/66* (2006.01)
*A61F 2/54* (2006.01)

(52) U.S. Cl.
USPC .................... 623/25; 623/24; 623/57; 623/58

(58) Field of Classification Search
USPC .................................................... 623/24, 57
See application file for complete search history.

(56) References Cited

U.S. PATENT DOCUMENTS

| | | | |
|---|---|---|---|
| 3,866,246 A | 2/1975 | Seamone et al. | |
| 4,558,704 A | 12/1985 | Petrofsky | |
| 4,808,187 A | 2/1989 | Patterson et al. | |
| 5,413,611 A | 5/1995 | Haslam, II et al. | |
| 6,344,062 B1 * | 2/2002 | Abboudi et al. | 623/24 |
| 7,922,773 B1 * | 4/2011 | Kuiken | 623/24 |
| 2004/0078091 A1 | 4/2004 | Elkins | |
| 2005/0192677 A1 * | 9/2005 | Ragnarsdottir et al. | 623/24 |
| 2006/0167564 A1 * | 7/2006 | Flaherty et al. | 623/57 |
| 2008/0146981 A1 | 6/2008 | Greenwald et al. | |

FOREIGN PATENT DOCUMENTS

| | | |
|---|---|---|
| EP | 0145504 A2 | 6/1985 |
| EP | 1043003 A1 | 10/2000 |
| GB | 2444679 A | 6/2008 |
| GB | 0916895.6 | 3/2010 |
| GB | PCT/GB2010/051529 | 1/2011 |

(Continued)

*Primary Examiner* — David Isabella
*Assistant Examiner* — Jacqueline Woznicki
(74) *Attorney, Agent, or Firm* — K&L Gates LLP

(57) ABSTRACT

The invention provides a prosthetic apparatus (10) and method of operating the same. The prosthetic apparatus (10) includes an upper limb prosthesis (12) comprising at least one mechanically operable digit (14) and at least one sensor configured to be disposed on the user. The at least one sensor being operative to sense a path described by the sensor during movement thereof by the user and to provide a sensed path output in dependence upon the path. The apparatus (10) also includes a processor (24) operative to provide for actuation of the at least one digit (14) in dependence on the sensed path output having a predetermined characteristic and such that the at least one digit (14) moves in a predetermined fashion.

21 Claims, 1 Drawing Sheet

(56) References Cited

FOREIGN PATENT DOCUMENTS

| WO | WO 00/69375 | 11/2000 |
| WO | 2006/069264 | 6/2006 |
| WO | WO 2006/069264 A1 | 6/2006 |
| WO | WO 2007/127973 A2 | 11/2007 |
| WO | 2008/044207 | 4/2008 |
| WO | WO 2008/044207 A2 | 4/2008 |
| WO | 2008/098059 | 8/2008 |
| WO | WO 2008/098059 A2 | 8/2008 |
| WO | WO 2008/098072 A2 | 8/2008 |
| WO | 2011/036473 | 3/2011 |
| WO | PCT/GB2010/051529 | 4/2012 |

* cited by examiner

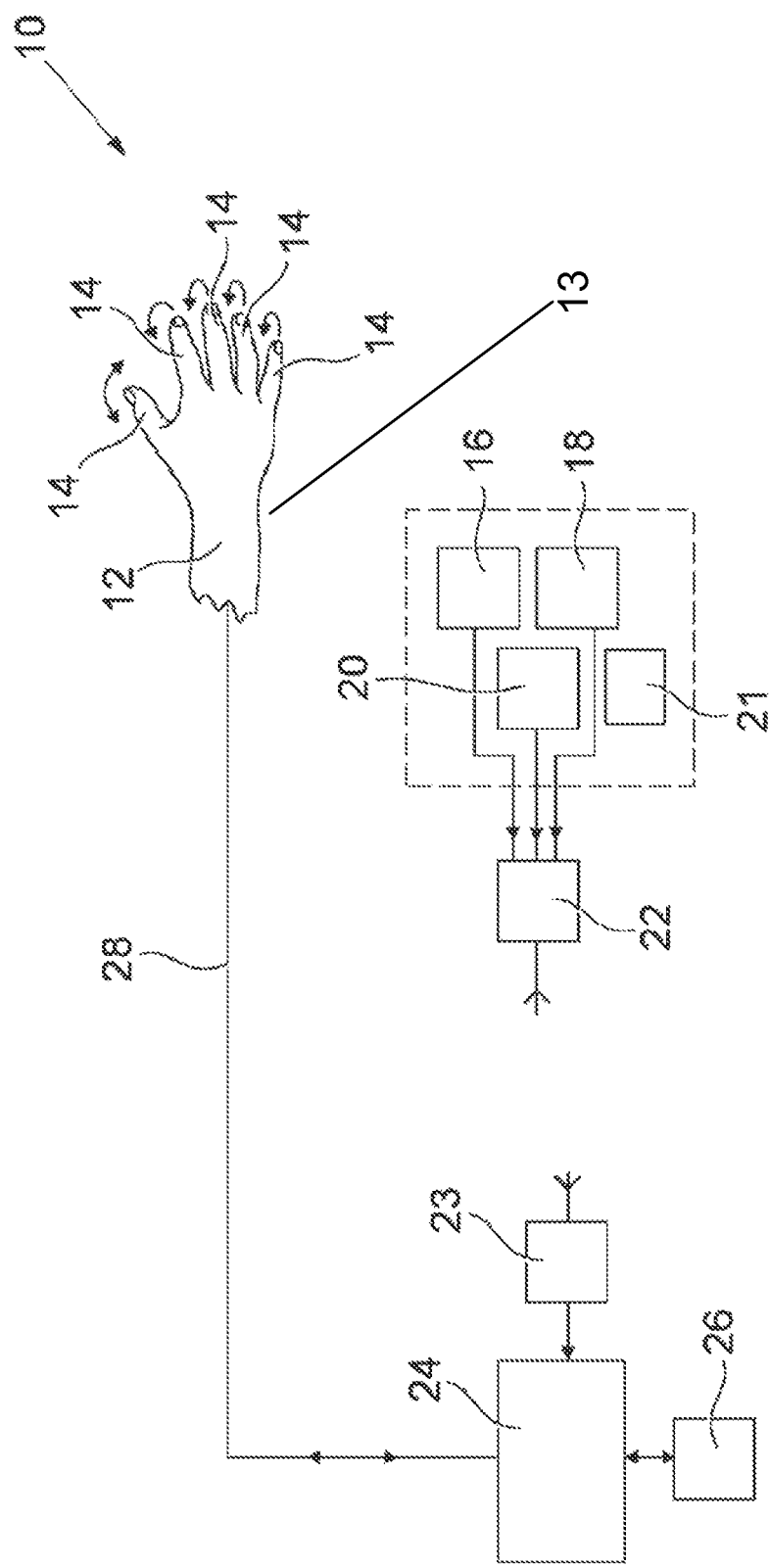

PROSTHETIC APPARATUS AND CONTROL METHOD

FIELD OF THE INVENTION

The present invention relates to prosthetic apparatus comprising an upper limb prosthesis and a method of operating the same.

STATEMENT OF INVENTION

According to a first aspect of the present invention, there is provided prosthetic apparatus for a user, the apparatus comprising:
- an upper limb prosthesis comprising at least one mechanically operable digit;
- at least one sensor configured to be disposed on the user, the at least one sensor being operative to sense a path described by the sensor during movement thereof by the user and to provide a sensed path output in dependence upon the path; and
- a processor operative to provide for actuation of the at least one digit in dependence on the sensed path output having a predetermined characteristic and such that the at least one digit moves in a predetermined fashion.

The term "path" used above is considered in the present invention to mean a continuous curve that connects two or more points in space. In the present invention the shape of the curve (or path) is dependent upon the movement of the sensor by the user.

The term "sensed path output" may be considered as a signal which is representative of the path. That is, the sensed path output may be a signal which includes one or more parameters which are characteristic of the shape of the curve (or path).

In use, the prosthetic apparatus of the present invention provides for movement in a predetermined fashion of at least one digit of the upper limb prosthesis in dependence on a predetermined movement of the at least one sensor. Hence, the user can, for example, move a part of his or her anatomy to which the sensor is attached in a predetermined fashion to move the at least one digit in a predetermined fashion. If the sensed path output produced by the sensor does not have a predetermined characteristic recognized by the processor no actuation of the digit is performed. That is, if the sensed path is not included within, for example, a library of predetermined paths known to the processor, no movement of the digit is performed.

Thus, in the present invention the at least one digit can be moved without the user actuating the at least one digit. For example, the present invention could be configured for a teacher such that a prosthetic index finger of the upper limb prosthesis is automatically extended when the teacher raises his arm in the direction of a blackboard. This is in contrast to known approaches where, for example, digits can be moved by flexing muscles in a residual part of an upper limb to generate electrical signals which are sensed and used to provide for movement of the at least one digit. Such known approaches typically include myoelectric prostheses and do not sense movement. Furthermore, such known approaches do not provide movement of a digit of a prosthesis as a result of a predetermined movement of a sensor.

More specifically, the processor may be operative to provide for actuation of the at least one digit such that the at least one digit moves in an acyclic fashion. Thus, the at least one digit may not perform a repeated action.

Alternatively or in addition, the processor may be operative in dependence on an acyclic movement of the sensor. For example, the prosthetic apparatus may be operative with an acyclic movement, such as a single sweep of an arm, in contrast with a cyclic movement, such as movement of a leg when walking.

Alternatively or in addition, the at least one sensor may be operative to sense movement of the sensor in each of three mutually orthogonal directions, i.e. in the x, y and z directions.

Alternatively or in addition, the at least one sensor may comprise an accelerometer. The accelerometer may be operative to sense the inclination of movement.

Alternatively or in addition, the at least one sensor may comprise a magnetometer. The magnetometer may be operative to sense the azimuth (i.e. compass direction) of movement.

Alternatively or in addition, the at least one sensor may comprise a gyroscope. The gyroscope may be operative to sense a direction of movement. When the at least one sensor comprises a gyroscope and an accelerometer, position, orientation and velocity may be sensed. Where the at least one sensor comprises a magnetometer in addition to a gyroscope and an accelerometer, orientation and velocity with respect to a direction relative to the Earth's magnetic poles, e.g. compass north, may be determined.

Alternatively or in addition, the at least one sensor may be operative to sense movement with respect to gravity.

Alternatively or in addition, the at least one sensor may be operative to sense at least one of: acceleration; velocity; deceleration; distance traveled; trajectory; start position; end position; and orientation.

Alternatively or in addition, the processor may be further operative to determine at least one parameter based on the sensed path output. The at least one parameter may comprise a plurality of sets of coordinates representing the changing position of the at least one sensor over time. Thus, the at least one parameter may represent the path described by the sensor during movement by the user. Each set of coordinates may comprise at least two mutually orthogonal coordinate elements, such as x, y and z coordinates.

Alternatively or in addition, the at least one sensor may, in use, be attached to the upper limb prosthesis. More specifically, the at least one sensor may be configured to be attached to the upper limb prosthesis. Hence, the at least one sensor may be operative to sense a path described by the arm to which the upper limb prosthesis is attached.

Alternatively or in addition, the at least one sensor may be configured to be attached to the user at a location on the user's anatomy spaced apart from the location at which the upper limb prosthesis is attached to the user. More specifically, the at least one sensor may be configured to be releasably attached to the user's anatomy, e.g. by means of a strap of the kind used on a watch so that the at least one sensor may be attached to the other wrist or an ankle of the user. Thus, for example, if the user is wearing the prosthesis on his right arm and the at least one sensor is attached to his left wrist, a predetermined movement of the user's left arm or rotation of the wrist may be used to actuate movement of the at least one digit on the right arm. The at least one sensor may be attached to another part of the anatomy having regards to limits on mobility of the user. For example, at least one sensor may be attached to the user's shoulder or elbow so that a predetermined movement of this part of the user's anatomy may be used to actuate movement of the at least one digit on the right arm.

More specifically, the prosthetic apparatus may be configured for wireless communication between the upper limb prosthesis and the at least one sensor. The processor may form part of the upper limb prosthesis. For example, wireless communication between the upper limb prosthesis and the at least one sensor may be provided by communications devices in the upper limb prosthesis and the at least one sensor that are operative according to, e.g. the Bluetooth protocol.

Alternatively or in addition, movement of the at least one digit in response to actuation by the processor may constitute a discrete movement.

More specifically, the processor may be further operative to provide for actuation of the at least one digit to perform at least one further discrete movement. For example, the at least one movement may perform a series of discrete movements, such as first discrete movement from a clenched to open palm disposition followed by a second discrete movement of the finger and thumb together such that, for example, an object may be grasped.

Alternatively or in addition, the upper limb prosthesis may further comprise a movable wrist and the processor may be further operative to provide for actuation of the movable wrist in dependence on the sensed path output having the predetermined characteristic. For example, the wrist may be rotated. Thus, for example, the upper limb prosthesis may be operated such that the digits move from a clenched position to an open palm position followed by a wrist rotation to thereby provide for a waving action.

Alternatively or in addition, the operation of the processor to provide for actuation of the at least one digit may depend on an initiating operation. The initiating operation may be user actuated. The initiation operation may prevent an unintended actuation of the at least one digit in dependence on the sensed path output.

More specifically, the initiating operation may comprise actuation of at least one part, e.g. digit, of the upper limb prosthesis. Actuation of the at least one part may comprise the pinching together of a prosthetic thumb and forefinger, e.g. in response to the user flexing muscles in a residual part of his upper limb to generate electrical signals which are sensed and used to provide for the pinching together movement.

Alternatively or in addition, the prosthetic apparatus may further comprise global position determining apparatus, such as a Global Positioning System (GPS) receiver. In use, the global position determining apparatus may be operative to provide global position datum for the data provided by the at least one sensor.

Alternatively or in addition, the prosthetic apparatus may be configured to set a datum position for the at least one sensor. More specifically, the prosthetic apparatus may comprise a user actuated datum setting arrangement that is operative to cause data from the at least one sensor to be stored as a datum. For example, the user may allow the arm bearing the at least one sensor to hang beside his side and may actuate the datum setting arrangement to record this disposition of his arm as the datum. The datum setting arrangement may comprise a selector, such as a switch, that is user operable. Alternatively or in addition, the datum setting arrangement may comprise a sensor, e.g. an accelerometer, that is operative to sense a predetermined action, such as the tapping of the prosthesis three times.

Alternatively or in addition, the processor may be operative to analyze the sensed path output to determine if the sensed path output has the predetermined characteristic.

More specifically, analyzing the sensed path output may comprise determining at least one sensed parameter from the sensed path output and comparing the at least one sensed parameter with at least one stored parameter to determine if the sensed path output has the predetermined characteristic. Thus, the prosthetic apparatus may further comprise data storage.

More specifically, the processor may store at least one predetermined movement for the at least one digit. The at least one predetermined movement may, for example, be stored as a digital representation of one or more control signals for actuating the at least one digit. Therefore, the processor may be operative to output the at least one predetermined movement, e.g. as at least one control signal, to provide for actuation of the at least one digit.

Alternatively or in addition, the processor may store a plurality of predetermined characteristics and a corresponding different movement for the at least one digit for each predetermined characteristic. For example, the processor may store a first predetermined characteristic corresponding to movement of the limb of the user bearing the prosthesis from a by the side of the body position to an outstretched and forward directed arm position and a first movement corresponding to a movement of a prosthetic index finger from a contracted position to an extended position. Such a pair of predetermined characteristic and corresponding movement could be used, for example, by a teacher when he wishes to point at the blackboard. The processor may also store a second predetermined characteristic corresponding to movement of the limb from a by the side of the body position to an outstretched and upwardly directed arm position and a second movement corresponding to a movement of all four fingers and thumb from a clenched arrangement to an extended, open palm arrangement. Such a pair of predetermined characteristic and corresponding movement could be used, for example, by the teacher when he wishes to reach up to a shelf and take hold of a book.

Each predetermined characteristic may, for example, be stored as a digital representation of one or more parameters representing the predetermined characteristic. Each predetermined movement may, for example, be stored as a digital representation of one or more control signals for actuating the at least one digit.

More specifically, the processor may be operative to determine if the sensed path output corresponds to one of the plurality of predetermined characteristics. If the sensed path output corresponds to one of the plurality of predetermined characteristics the processor may be operative to select the corresponding predetermined movement to provide for actuation of the at least one digit in accordance with the selected predetermined movement.

Alternatively or in addition, the upper limb prosthesis may comprise a plurality of digits, e.g. four fingers and a thumb. The plurality of digits may be independently movable. The plurality of digits may be independently actuated. The upper limb prosthesis may be of the kind described in WO 2007/063266 (to the present applicant) having independently movable digits that are actuated by means of a motor mounted in each digit.

According to a second aspect of the present invention, there is provided a method of operating prosthetic apparatus comprising an upper limb prosthesis, the method comprising:

operating at least one sensor disposed on a user of the prosthetic apparatus to sense a path described by the sensor during movement thereof by the user and to provide a sensed path output in dependence upon the path; and operating a processor to provide for actuation of at least one digit of the upper limb prosthesis in dependence on the sensed path output having a predetermined characteristic and such that the at least one digit moves in a predetermined fashion.

More specifically, the method may further comprise:

moving at least one sensor disposed on a user of the prosthetic apparatus such that the at least one sensor describes a predetermined path, the at least one sensor operating to provide a sensed path output in dependence thereon;

operating a processor to determine a predetermined characteristic from the sensed path output and to store the predetermined characteristic;

moving the at least one digit in a predetermined fashion; and operating the processor to store data (e.g. in the form of a digital representation of one or more control signals for actuating the at least one digit) corresponding to the movement of the at least one digit in the predetermined fashion.

Thus, the further steps may be used to configure the prosthetic apparatus for at least one pair of: predetermined characteristic of movement of the sensor; and movement of the at least one digit in a predetermined fashion. The further steps may be repeated for a plurality of such pairs.

More specifically, the method may further comprise putting the prosthetic apparatus in a configuration mode whereby the prosthetic apparatus may be configured for at least one pair of: predetermined characteristic of movement of the sensor; and movement of the at least one digit in a predetermined fashion. The prosthetic apparatus may be put in the configuration mode by, for example, a user operable switch on the upper limb prosthesis.

Alternatively or in addition, the method may further comprise actuating the prosthetic limb by means of myoelectric signals. More specifically, myoelectric signals may be used to perform a further discrete movement, such as a gripping movement following actuation of the at least one digit in dependence on the sensed path output having a predetermined characteristic to, for example, allow for an object to be gripped and lifted.

Further embodiments of the second aspect of the present invention may comprise one or more features of the first aspect of the present invention.

According to a further aspect of the present invention, there is provided prosthetic apparatus for a user, the apparatus comprising:

an upper limb prosthesis comprising at least one mechanically operable digit;

at least one sensor configured to be disposed on the user, the at least one sensor being operative to sense motion of the sensor caused by movement by the user and to provide a sensed motion output in dependence thereon; and a processor operative to provide for actuation of the at least one digit in dependence on the sensed motion output having a predetermined characteristic and such that the at least one digit moves in a predetermined fashion.

More specifically, the at least one sensor may be operative to sense a path described by the sensor during movement by the user and to provide a sensed path output in dependence thereon and the processor may be operative to provide for actuation of the at least one digit in dependence on the sensed path output.

Further embodiments may comprise one or more features of the first aspect of the present invention.

BRIEF DESCRIPTION OF THE DRAWINGS

The present invention will now be described by way of example only with reference to the following drawings, of which:

FIG. 1 is a representation of prosthetic apparatus according to the invention.

SPECIFIC DESCRIPTION

The prosthetic apparatus 10 according to a first embodiment of the invention is shown in FIG. 1. The prosthetic apparatus 10 comprises an upper arm prosthesis 12 having four fingers and a thumb 14 (each of which constitutes a digit). Each of the four fingers and the thumb are independently movable by means of an electric motor provided in each finger and the thumb. Reference should be made to WO 2007/063266 for a full description of a hand prosthesis having independently actuated digits. Each digit is actuated in accordance with known approaches by the user of the prosthesis 12 flexing muscles in the residual part of the arm to generate signals which are sensed and used to provide electrical power to drive motors in the digits. The upper arm prosthesis also has a movable wrist joint 13 that is actuated by means of an electric motor in accordance with known approaches. The prosthetic apparatus 10 also comprises a three axis accelerometer 16, a gyroscope 18 and a magnetometer 20 (which together constitute at least one sensor). The prosthetic apparatus 10 further comprises a GPS receiver 21, which is operative to provide a datum location for the sensors in world coordinates. Output signals from the accelerometer 16, the gyroscope 18, the magnetometer 20 and the GPS receiver 21 are pre-processed before being transmitted by means of a wireless transmitter 22 operating in accordance with the Bluetooth protocol. Where the signal from a sensor is analog, pre-processing also involves analog-to-digital conversion. The signal transmitted from the wireless transmitter 22 is received by a wireless receiver 23 before being received in a processor 24, such as an embedded microprocessor. Data storage 26, such as static and volatile memory, is in electrical communication with the processor. The data storage 26 is used to store firmware, predetermined data and temporary data created during operation of the prosthetic apparatus 10. The processor has an output 28 that is in electrical communication with the prosthesis 12. The form of electrical signal transmitted on the processor output 28 depends on the form of digit control electronics provided in the prosthesis 12. For example, the processor output 28 is provided by a buffered digital output from the processor if the digits are controlled by means of a stream of digital data. On the other hand, if the digits are controlled by an analog signal, the processor output 28 is provided by an output from a digital-to-analogue converter on board the processor 24. The selection of a processor, data storage and wireless communications devices and the design of circuitry in accordance with the aforegoing description will be readily within the grasp of the person of ordinary skill.

The processor 26, the data storage 26 and the wireless receiver 23 form part of the prosthesis 12. The accelerometer 16, the gyroscope 18, the magnetometer 20, the GPS receiver 21 and the wireless transmitter 22 are provided within an enclosure that is movable with respect to the prosthesis. The enclosure is provided with an attachment device, such as watch type strap, so that the enclosure can be attached to a part of the user's anatomy, such as the ankle or other arm, spaced apart from the prosthesis 12. The selection of the accelerometer 16, the gyroscope 18, the magnetometer 20 and the GPS receiver 21 and the design of whatever supporting circuitry may be required will be readily within the scope of the design skills of the person of ordinary skill.

In a second embodiment, the prosthetic apparatus 10 lacks the wireless transmitter 22 and receiver 23. In this embodiment the three sensors and the GPS receiver form part of the prosthesis 12. Hence, there is no need for wireless transmission of sensor data. Therefore, electrical outputs from the accelerometer 16, the gyroscope 18, the magnetometer 20 and the GPS receiver 21 are electrically connected to the processor 24.

Operation of the first embodiment will now be described. The user of the prosthesis 12 attaches the enclosure containing the three sensors 16, 18, 20 to the wrist of the arm that is not supporting the prosthesis. When the user wishes to employ the present invention, he executes an initiating operation, such as the pinching together of the index finger and the thumb of the prosthesis 12, which causes transmission of an initiating signal to the processor 24. Upon reception of the initiating signal by the processor 24, the processor 24 operates a process in accordance with firmware resident in the data storage 26 whereby the processor is operative to receive data from the wireless receiver 23. When the user executes a predetermined movement with the arm bearing the three sensors, such as moving his arm from a downwardly pointing and beside the body position to a position where his arm is extended forwards of his body, the three sensors are operative to provide output signals, which are received by the processor 24. More specifically, the three axis accelerometer generates a series of time spaced sets of x, y and z data values and each of the magnetometer and the gyroscope generates a series of time spaced data values. The processor is operative on the received data to determine from the received data a series of time spaced sets of x, y and z world coordinates that represent the changing position of the three sensors during execution of the predetermined movement. The processor is then operative to determine on the basis of the series of time spaced sets of x, y and z world coordinates whatever parameters are required to characterize the path of the arm during execution of the predetermined movement. Parameters include: the start position and the stop position of the three sensors; the trajectory followed and the distance traveled by the three sensors; the orientation of the three sensors; and parts of the path in which there is acceleration and deceleration. The accelerometer provides, amongst other things, information regarding direction with respect to gravity and the magnetometer provides information regarding direction with respect to magnetic North.

The processor compares the determined parameters with a number of predetermined, stored sets of parameters that correspond respectively to different predetermined movements of at least one digit of the prosthesis 12, i.e. the apparatus further comprises a library of predetermined, stored sets of parameters that correspond respectively to different predetermined movements of at least one digit of the prosthesis 12. For example, the predetermined, stored sets of parameters may correspond to a pointing gesture, an open palm gesture with wrist rotation and a clenched fist gesture. For the present example, the determined parameters are found to correspond to the predetermined, stored set of parameters corresponding to the pointing gesture. Therefore, the processor is operative to determine from stored data the command signals required to cause the index finger to move from a contracted position to a fully extended position and to transmit the command signals over the processor output line 28 to actuate the index finger. The other gestures, i.e. the open palm gesture with wrist rotation and the clenched fist gesture, may be invoked by the user executing different predetermined movements of his sensor enclosure bearing arm, e.g. a rotating movement or a flexing of his lower arm towards his upper arm. Thereafter the user can actuate the moving parts of the prosthetic limb, e.g. the wrist and the digits, by means of the known myoelectric signal actuation approach. In forms of the invention, the prosthetic apparatus may be operable to perform a series of actions in dependence on a predetermined movement. For example, a first action may involve the digits being moved from a clenched to an open palm disposition and a second action may involve the rotation at the wrist.

The second embodiment operates in the same manner as the first embodiment with the exception that it is the movement of the prosthesis bearing arm in a predetermined manner that invokes movement of at least one digit to make, for example, one of the gestures mentioned above.

The accelerometer, magnetometer and the gyroscope provide position data that is of a relative nature. A datum for the relative position data is provided in one form by the GPS receiver. In another form, the prosthetic apparatus comprises a user actuated datum setting arrangement that is operative to cause data from the at least one sensor to be stored as a datum. More specifically, the user actuated datum setting arrangement comprises the accelerometer. In use, the user allows the arm bearing the at least one sensor to hang beside his side to establish a datum disposition. The user then provides for storage of position data as the datum by actuating the accelerometer by tapping the prosthesis three times.

The first and second embodiments are configured in respect of pairs of corresponding movements of the sensor enclosure and predetermined movements of the prosthesis digits as follows. The processor is put into a configuration mode by the user, e.g. by operating a switch, and the user executes a new movement of his arm. The processor is operative to store characteristic parameters of the new movement. The user then causes the digits to move in accordance with a new fashion. The processor is then operative to determine and store control signals corresponding this new digit movement and to associate the stored control signals with the stored characteristic parameters. The user then operates the prosthesis to leave the configuration mode. The prosthetic apparatus is thus configured to provide for a further different predetermined movement of the prosthesis digits in response to a further predetermined movement of the user's arm.

The processor may also be pre-programmed by a prosthetist to store one or more predetermined movements of the prosthesis required by the user. In this example the prosthetist will work with the user to compile a list of actions commonly performed by the user. This may involve use of a graphical user interface (GUI) to demonstrate, capture and store each action, or "pathway". The actions may comprise a discrete movement or a number of discrete movements. In this manner the apparatus would therefore come pre-loaded with one or more bespoke actions common to the user.

The invention claimed is:

1. Prosthetic apparatus for a user, the apparatus comprising: an upper limb prosthesis comprising at least one mechanically operable digit; at least one sensor configured to be disposed in the upper limb prosthesis, the at least one sensor being operative to sense a path traversed by the sensor during movement of the upper limb prosthesis in three dimensional space by the user and to provide a sensed path output in response to the path in three dimensional space; and a processor autonomously operative to actuate the at least one digit in response to the sensed path output having a predetermined characteristic and such that the at least one digit moves in a predetermined fashion in response to the predetermined characteristic, without further user intervention and wherein muscle signals are not sensed by the at least one sensor.

2. Prosthetic apparatus according to claim 1, in which the processor is operative in dependence on an acyclic movement of the upper limb prosthesis.

3. Prosthetic apparatus according to claim 1, in which the processor is operative to provide for actuation of the at least one digit such that the at least one digit moves in an acyclic fashion.

4. Prosthetic apparatus according to claim 1, in which the at least one sensor is operative to sense movement of the sensor in each of three mutually orthogonal directions.

5. Prosthetic apparatus according to claim 1 in which the at least one sensor comprises an accelerometer operative to sense an inclination of movement.

6. Prosthetic apparatus according to claim 1, in which the at least one sensor comprises a magnetometer operative to sense an azimuth of movement.

7. Prosthetic apparatus according to claim 1, in which the at least one sensor comprises a gyroscope operative to sense a direction of movement.

8. Prosthetic apparatus according to claim 1, in which the at least one sensor is operative to sense movement with respect to gravity.

9. Prosthetic apparatus according to claim 1, in which the at least one sensor is operative to sense at least one of: acceleration, velocity, deceleration, distance traveled, trajectory, start position, end position, and orientation of the at least one sensor.

10. Prosthetic apparatus according to claim 1, in which the processor is further operative to determine at least one parameter based on the sensed path output, the at least one parameter comprising a plurality of sets of coordinates representing the changing position of the at least one sensor over time.

11. Prosthetic apparatus according to claim 1, in which the prosthetic apparatus is configured for wireless communication between the controller of upper limb prosthesis and the at least one sensor.

12. Prosthetic apparatus according to claim 1, in which movement of the at least one digit in response to actuation by the processor constitutes a discrete movement.

13. Prosthetic apparatus according to claim 12, in which the processor is further operative to provide for actuation of the at least one digit to perform at least one further discrete movement.

14. Prosthetic apparatus according to claim 1, in which the upper limb prosthesis further comprises a movable wrist and the processor is further operative to provide for actuation of the movable wrist in dependence on the sensed path output having the predetermined characteristic.

15. Prosthetic apparatus according to claim 1, in which the operation of the processor to provide for actuation of the at least one digit depends on an initiating operation, the initiating operation being user actuated.

16. Prosthetic apparatus according to claim 15, in which the initiating operation comprises actuation of at least one part of the upper limb prosthesis.

17. Prosthetic apparatus according to claim 1, in which the prosthetic apparatus further comprises a global position determining apparatus operative to provide global position datum for the data provided by the at least one sensor.

18. Prosthetic apparatus according to claim 1, in which the prosthetic apparatus is configured to set a datum position for the at least one sensor.

19. Prosthetic apparatus according to claim 1, in which the processor is operative to analyze the sensed path output to determine if the sensed path output has the predetermined characteristic.

20. Prosthetic apparatus according to claim 19, in which analyzing the sensed path output comprises determining at least one sensed parameter from the sensed path output and comparing the at least one sensed parameter with at least one stored parameter to determine if the sensed path output has the predetermined characteristic.

21. Prosthetic apparatus according to claim 1, in which memory of the processor stores a plurality of predetermined characteristics and instructions for a corresponding different movement for the at least one digit for each predetermined characteristic, the processor being operative to determine if the sensed path output corresponds to one of the plurality of predetermined characteristics, and if the sensed path output corresponds to one of the plurality of predetermined characteristics the processor being operative to select the corresponding predetermined movement to provide for actuation of the at least one digit in accordance with the selected predetermined movement.

* * * * *